(12) United States Patent
Adams

(10) Patent No.: US 7,811,228 B2
(45) Date of Patent: Oct. 12, 2010

(54) DISPOSABLE ENDOSCOPE SHEATH HAVING ADJUSTABLE LENGTH

(75) Inventor: Kenneth M. Adams, Jacksonville, MN (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 10/899,209

(22) Filed: Jul. 26, 2004

(65) Prior Publication Data

US 2006/0020165 A1    Jan. 26, 2006

(51) Int. Cl.
*A61B 1/00* (2006.01)

(52) U.S. Cl. .................. 600/121; 600/122; 600/123; 600/124; 600/125; 600/157

(58) Field of Classification Search ............. 600/121, 600/155–157
See application file for complete search history.

(56) References Cited

U.S. PATENT DOCUMENTS

| | | | |
|---|---|---|---|
| 4,327,735 A | | 5/1982 | Hampson |
| 4,449,532 A | * | 5/1984 | Storz .......................... 606/191 |
| 4,784,117 A | * | 11/1988 | Miyazaki .................... 600/114 |
| 4,905,082 A | * | 2/1990 | Nishigaki et al. ............ 348/73 |
| 5,051,824 A | * | 9/1991 | Nishigaki .................... 348/68 |
| 5,061,246 A | | 10/1991 | Anapliotis |
| 5,163,927 A | | 11/1992 | Woker et al. |
| 5,199,417 A | | 4/1993 | Muller et al. |
| 5,239,981 A | * | 8/1993 | Anapliotis ................... 600/122 |
| 5,665,073 A | | 9/1997 | Bulow et al. |
| 5,711,756 A | * | 1/1998 | Chikama ..................... 600/112 |
| 5,951,463 A | * | 9/1999 | Lombardi et al. ............ 600/162 |
| 5,989,183 A | | 11/1999 | Reisdorf et al. |
| 6,110,103 A | | 8/2000 | Donofrio |
| 6,447,446 B1 | | 9/2002 | Smith et al. |
| 6,558,379 B1 | | 5/2003 | Batchelor et al. |
| 6,579,277 B1 | | 6/2003 | Rabiner et al. |
| 6,589,165 B2 | * | 7/2003 | Bodor et al. ................. 600/172 |
| 6,605,036 B1 | | 8/2003 | Wild |
| 6,743,166 B2 | * | 6/2004 | Berci et al. .................. 600/120 |
| 7,029,436 B2 | * | 4/2006 | Iizuka et al. ................. 600/160 |
| 2002/0072652 A1 | | 6/2002 | Berci et al. |
| 2002/0147385 A1 | * | 10/2002 | Butler et al. ................. 600/114 |

FOREIGN PATENT DOCUMENTS

| | | |
|---|---|---|
| EP | 0 664 101 A1 | 7/1995 |
| FR | 2752032 | 2/1998 |

OTHER PUBLICATIONS

PCT Search Report mailed Nov. 15, 2005 (8 pgs.).

* cited by examiner

*Primary Examiner*—Matthew J Kasztejna
(74) *Attorney, Agent, or Firm*—Dicke, Billig & Czaja, PLLC

(57) ABSTRACT

A disposable endoscope sheath includes an extendable sleeve sized to accommodate an endoscope shaft having a viewing end. The extendable sleeve has a variable length. A distal portion of the sleeve is configured to direct irrigation fluid onto the viewing end of the endoscope to flush surgical debris from the viewing end of the endoscope.

31 Claims, 8 Drawing Sheets

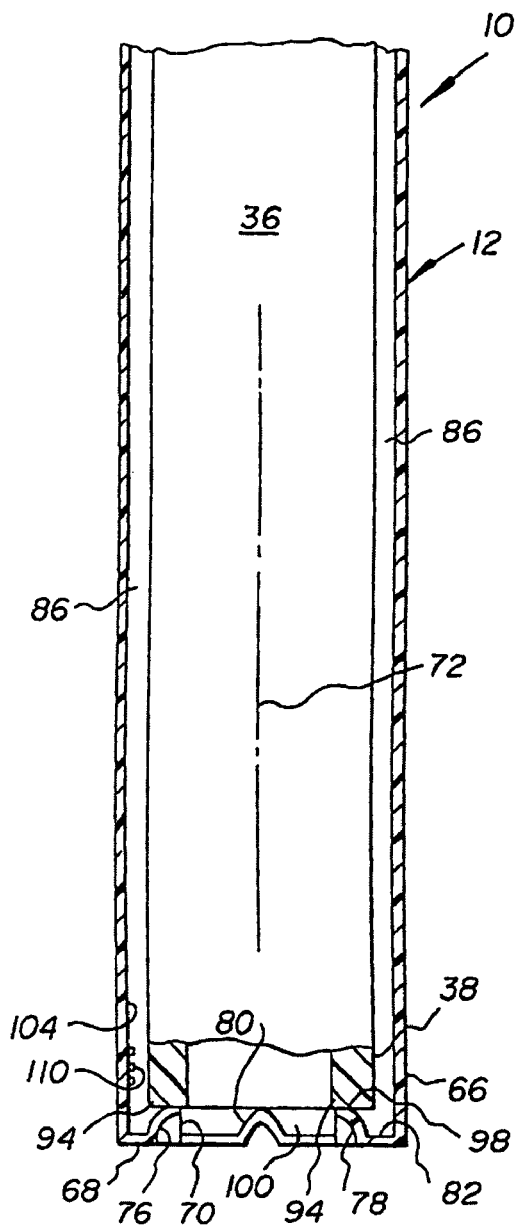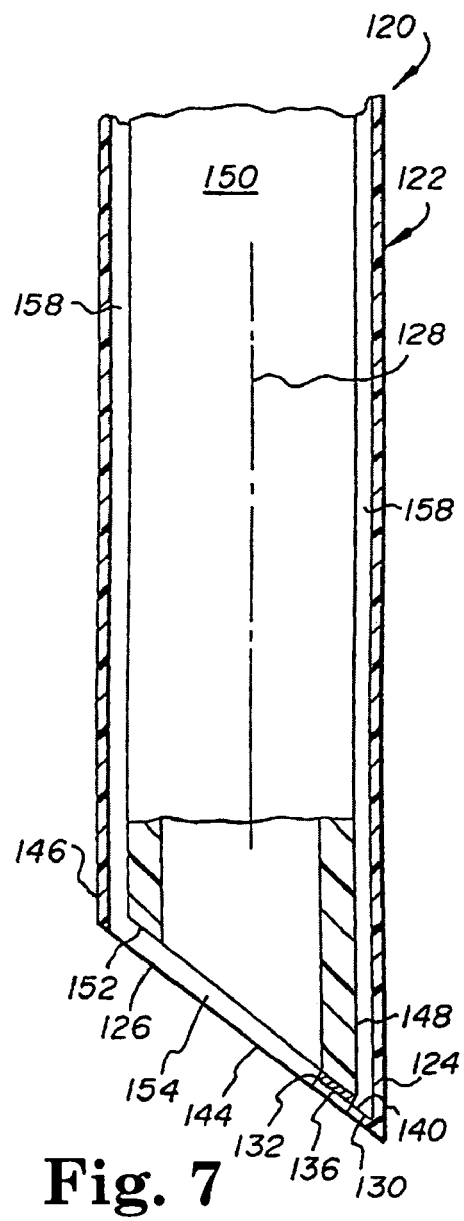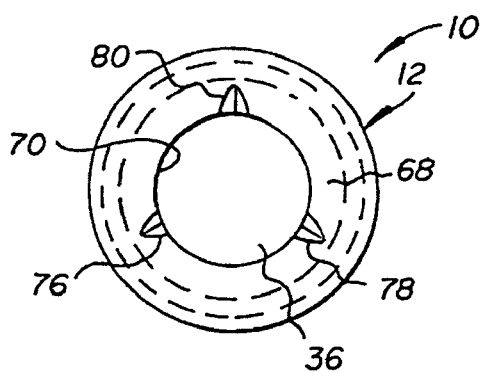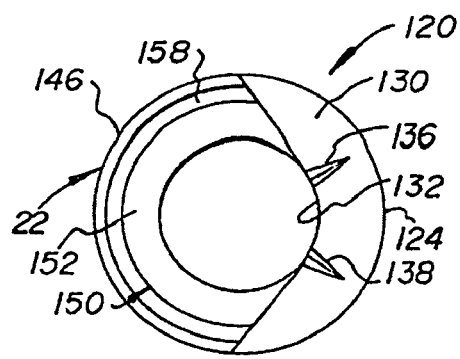
Fig. 5
Fig. 7
Fig. 6
Fig. 8

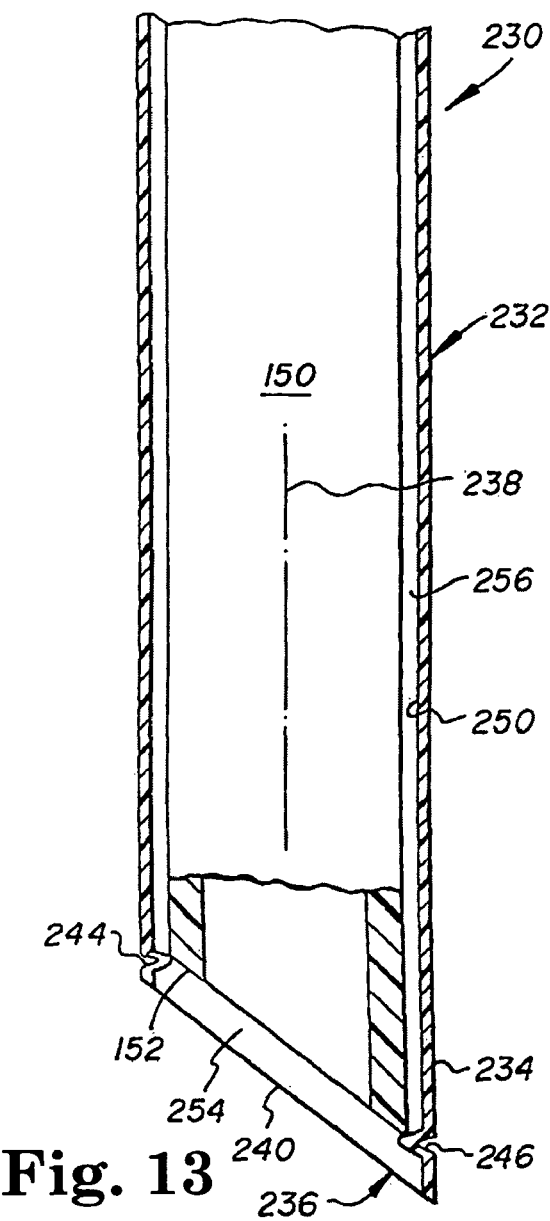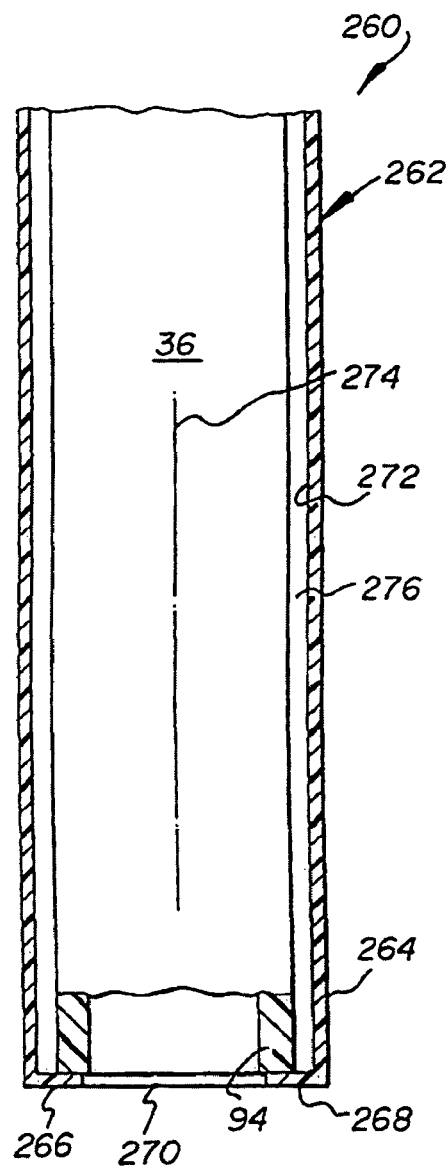
Fig. 13
Fig. 15
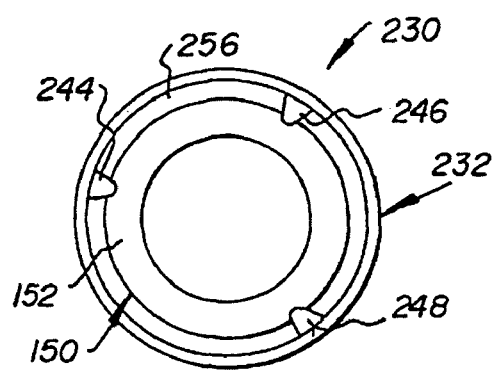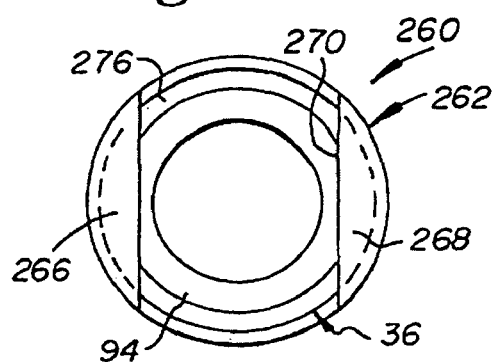
Fig. 14
Fig. 16

US 7,811,228 B2

DISPOSABLE ENDOSCOPE SHEATH HAVING ADJUSTABLE LENGTH

BACKGROUND OF THE INVENTION

The present invention is directed to disposable sheaths for endoscopes and more particularly to a low profile disposable sheath that provides effective flushing of surgical debris from the viewing end of an endoscope.

The term "surgical debris" is intended to refer to any body material such as blood or tissue that lands on the viewing end of an endoscope during surgery and obscures the field of view through the endoscope.

Endoscopes permit remote visual examination of a surgical site while a surgical procedure is being performed. During surgery, blood, tissue or other bodily material from the surgical site can splatter onto the viewing end of the endoscope and obscure the field of view through the endoscope.

In some instances it is necessary to remove the endoscope from the surgical site to clean the viewing end, which usually interrupts and undesirably prolongs a surgical procedure. Because of the inconvenience of removing and cleaning an endoscope during surgery, some surgeons prefer to use an endoscope with a sheath that has provision for flushing away any surgical debris that obscures the view through the endoscope. The sheath can include air tubes, water tube and suction tubes to flush away or suction out surgical debris from the viewing end of the endoscope. The irrigation, suction and air tubes on the endoscope sheath can add significant girth to the profile of the endoscope and require an incision of corresponding size to accommodate the endoscope and sheath.

Known endoscope sheaths, such as shown in U.S. Pat. Nos. 4,991,565 and 4,974,580, are usually custom fitted to the endoscope. Since many endoscopes are of different lengths, a diversity of different size sheaths are required to custom fit each different length of endoscope with a sheath. Large inventories of customized endoscope sheaths of different length are therefore generally maintained to ensure compatibility with each different endoscope. To reduce the need for large inventories of endoscope sheaths, sheaths having a fixed length but usable with a variety of endoscope lengths have been proposed, such as shown in U.S. Pat. Nos. 5,989,183 and 6,110,103. While reducing the required inventory of endoscope sheaths, a variety of sheath lengths are still required, as many different endoscope lengths are used, and large differences in length between the endoscope and the sheath can make operation and control of the endoscope and/or sheath difficult.

It is thus desirable to provide an endoscope sheath that has an adjustable length to accommodate a variety of different endoscope lengths, and that can effectively flush debris from the viewing end of the endoscope.

SUMMARY OF THE INVENTION

The invention described herein provides a novel disposable endoscope sheath having an adjustable length. In one embodiment according to the invention, the sheath includes an extendable sleeve sized to accommodate an endoscope shaft having a viewing end. The extendable sleeve has a variable length. A distal portion of the sleeve is configured to direct irrigation fluid onto the viewing end of the endoscope to flush surgical debris from the viewing end of the endoscope.

In accordance with one embodiment of the invention, the extendable sleeve includes a proximal sleeve section and a distal sleeve section. The proximal sleeve section and distal sleeve section are joined in a telescoping arrangement. The proximal sleeve section and the distal sleeve section are of generally circular cross section with predetermined inner diameters, such that an annular irrigation space of predetermined size is defined between the proximal sleeve section and the endoscope shaft, and between the distal sleeve section and the endoscope shaft when the proximal sleeve section and distal sleeve section receive the endoscope shaft. A sealing member is positioned between overlapping portions of the proximal sleeve section and the distal sleeve section to reduce or eliminate leaking of irrigation fluid at the telescoping joint. Irrigation fluid is directed from the irrigation space onto the viewing end of the endoscope.

BRIEF DESCRIPTION OF THE DRAWINGS

FIG. 5 is a sectional view of an embodiment of a distal sleeve section that forms a part of the disposable telescoping endoscope sheath.

FIG. 6 is an end view of the distal sleeve section of FIG. 5.

FIGS. 7-20 show distal sleeve sections in sectional view and end view employed in further embodiments of the disposable telescoping endoscope sheath; the sleeve housing and proximal sleeve section of FIGS. 1 and 2 being common to these embodiments is omitted for purposes of simplification.

Corresponding reference characters indicate corresponding parts throughout the several views of the drawings.

DETAILED DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figures 1, 2:
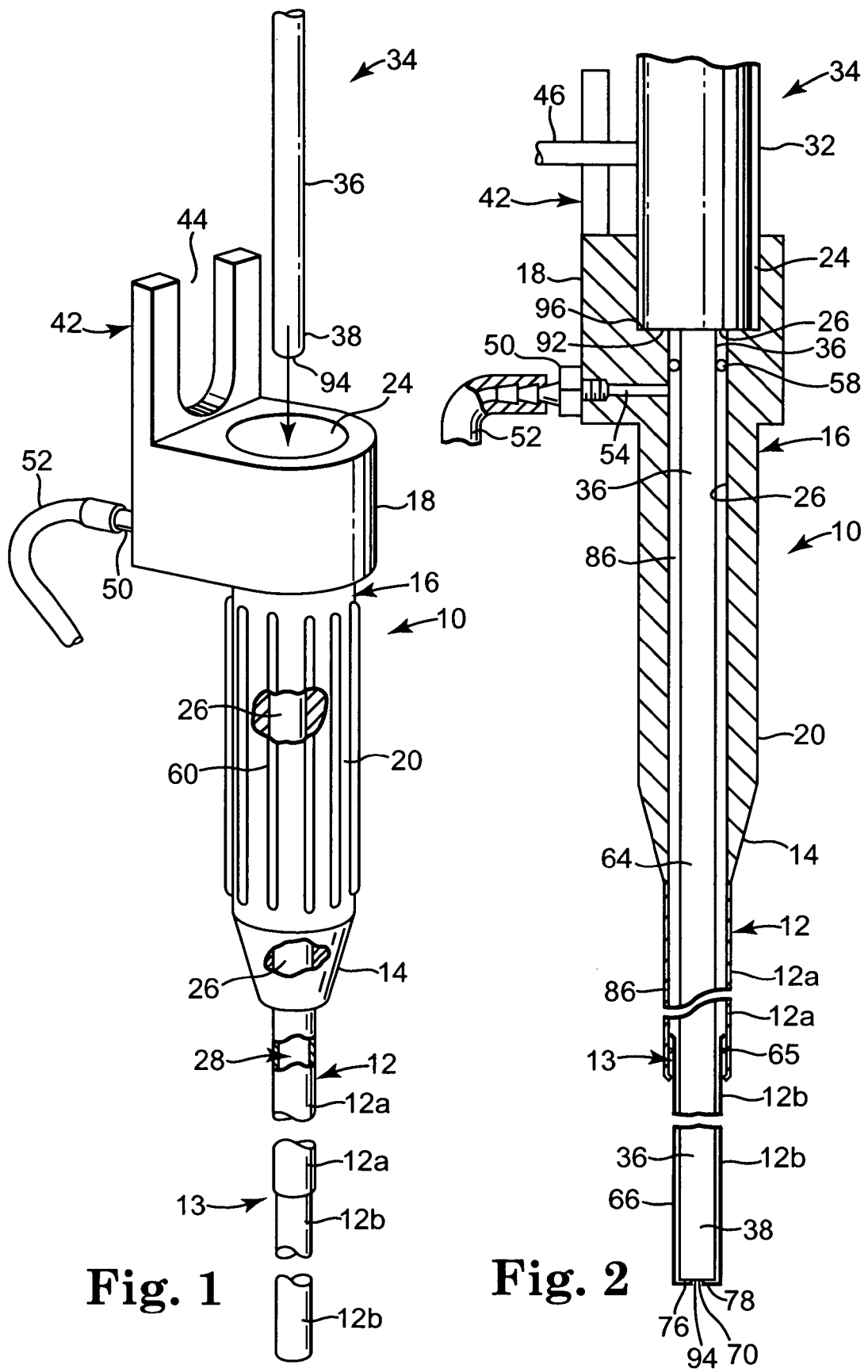
FIG. 1 is a simplified schematic perspective view of one embodiment of a disposable endoscope sheath including a telescoping sleeve member according to the invention, prior to reception of an endoscope.
FIG. 2 is a sectional view of the disposable endoscope sheath of FIG. 1, showing an endoscope being received in the sheath.

A disposable sheath incorporating one embodiment of the invention is generally indicated by the reference number 10 in FIG. 1. The sheath 10 includes an elongated telescoping sleeve member 12. Sleeve member 12 comprises a proximal sleeve section 12a and a distal sleeve section 12b joined at telescoping joint 13. The telescoping engagement of proximal sleeve section 12a and distal sleeve section 12b permits a continuous range of endoscope lengths to be accommodated by sleeve member 12, as the length of sleeve member 12 adjusts to match the length of the endoscope.

Proximal sleeve section 12a is joined to an end portion 14 of a sleeve housing 16 that is preferably formed of a plastic such as acrylonitrile-butadiene-styrene. The sleeve housing 16 includes a collar portion 18 with a depending body portion 20 that facilitates handling of the sheath 10.

A recess 24 in the collar portion 18 communicates with a bore 26 in the body portion 20, the bore 26 communicating with the hollow interior 28 (FIG. 1) of the sleeve member 12. Hollow interior 28 comprises interior 28a of proximal sleeve section 12a, and interior 28b of distal sleeve section 12b. As shown in FIG. 2, the recess 24 is adapted to receive a housing 32 of an endoscope 34. A shaft 36 of the endoscope 34 is insertable in the bore 26 and in the hollow interior 28 of the sleeve member 12. The recess 24 can be of any shape that complements the shape of the endoscope housing 32. Although not shown, the endoscope shaft 36 contains a light transmitting member and a lens, the lens being provided at a distal end portion 38 of the shaft 36.

The collar portion 18 further includes an upwardly extending yoke member 42 with a mouth 44 for securely holding the endoscope housing light port 46 to prevent rotation of the shaft 36 within sleeve member 12.

An irrigation fitting 50 joined to the collar portion 18 supports an irrigation tube 52. The tube 52 communicates with the bore 26 in the body portion 20 through a fluid passage 54 in the collar portion 18. An O-ring 58 in the collar portion 18 is adapted to surround the endoscope shaft 36 to prevent fluid regression from the bore 26 into the recess 24. Grip assist elements 60 are formed on the body portion 20 to facilitate manual handling thereof.

The proximal sleeve section 12a and distal sleeve section 12b are of generally tubular shape preferably formed of thin-walled metal or plastic having a wall thickness of approximately 0.001 to 0.012 inches. A fully open proximal end 64 of the proximal sleeve section 12a is bonded or otherwise secured within the bore 26 at the end 14 of the body portion 20 to form a leak-tight fit.

It should be noted that the body portion 20 primarily facilitates handling of the sheath 10 and, if desired, can be omitted to save material. Thus the proximal sleeve section 12a can be joined directly to the collar portion 18, resulting in an abbreviated bore 26.

Figure 3:
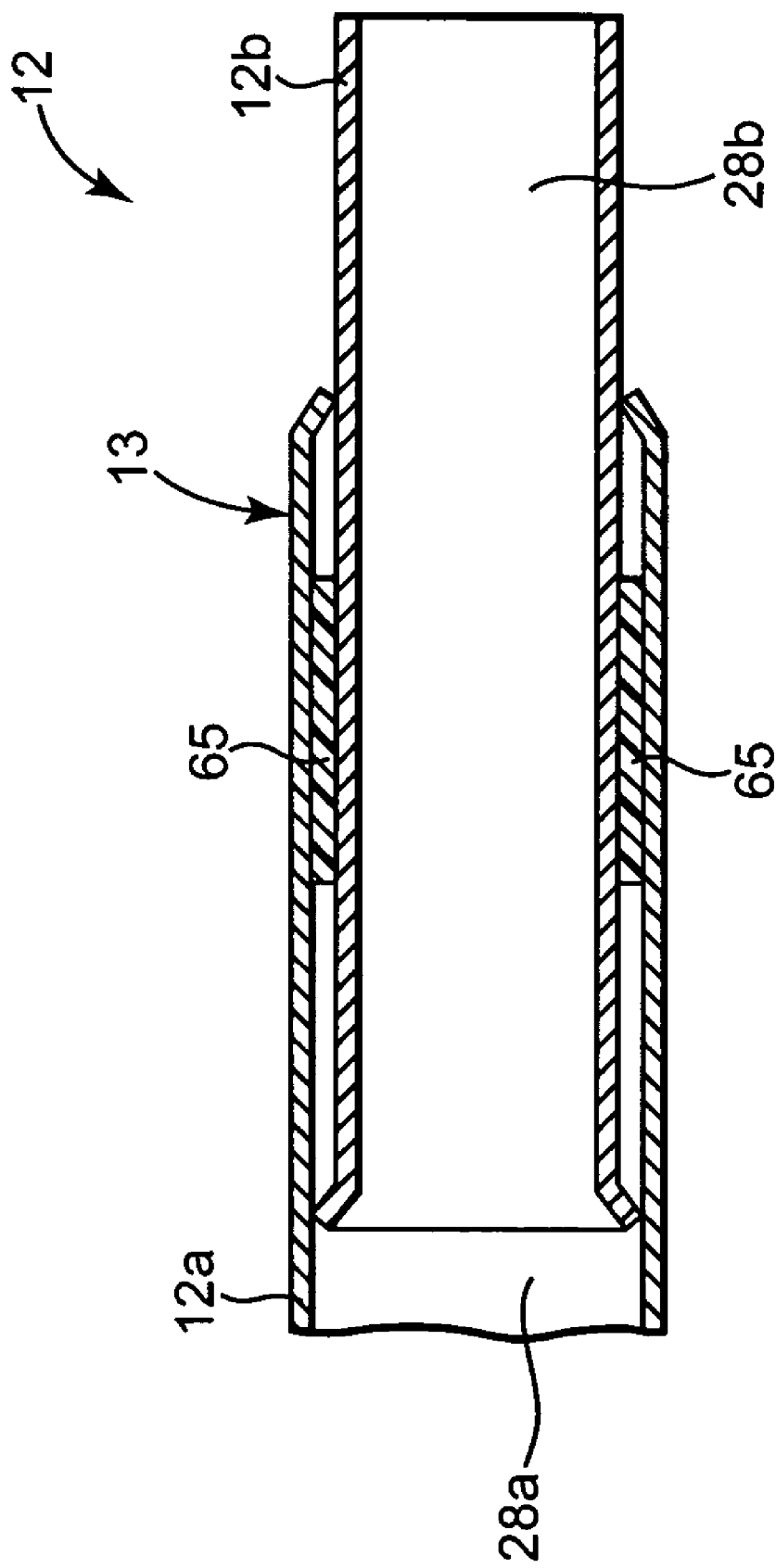
FIG. 3 is a greatly enlarged schematic sectional view showing one embodiment of a telescoping joint of the telescoping sleeve member according to the invention.

Referring to FIG. 3, the telescoping joint 13 of proximal sleeve section 12a and distal sleeve section 12b is shown greatly enlarged. For purposes of clarity, some dimensions of the joint 13 have been altered or exaggerated. As seen in FIG. 3, proximal sleeve section 12a is slightly larger in diameter than distal sleeve section 12b. In particular, distal sleeve section 12b has an inside diameter sized to accommodate a particular endoscope diameter, and proximal sleeve section 12a has an inside diameter sized to accommodate the outside diameter of distal sleeve section 12b.

Proximal sleeve section 12a and distal sleeve section 12b are disposed in telescoping engagement, with distal sleeve section 12b axially movable within proximal sleeve section 12a. When distal sleeve section 12b is fully inserted or retracted within proximal sleeve section 12a, the sleeve member 12 is at its shortest position. When distal sleeve section 12b is fully extended from proximal sleeve section 12a, the sleeve member 12 is at its longest position.

In a preferred embodiment, proximal sleeve section 12a and distal sleeve section 12b are prevented from overextension and separation by providing the distal end of proximal sleeve section 12a with a reduced inside diameter, and the proximal end of distal sleeve section 12b with an enlarged outside diameter, such that at the joint 13 the inside diameter of proximal sleeve section 12a is smaller than the outside diameter of distal sleeve section 12b. The diameters of proximal sleeve section 12a and distal sleeve section 12b may be altered by any suitable method, such as swaging if proximal sleeve section 12a and distal sleeve section 12b are made of metal, or molding in the desired profile if proximal sleeve section 12a and distal sleeve section 12b are made of plastic. Preferably, the proximal end of distal sleeve section 12b is also provided with an enlarged inside diameter, such that the proximal end of distal sleeve section 12b is shaped to guide an endoscope into the hollow interior 28b of distal sleeve section 12b.

In the embodiment of FIG. 3, the distal end of proximal sleeve section 12a and the proximal end of distal sleeve section 12b are sized to create a slip-fit between proximal sleeve section 12a and distal sleeve section 12b. Because of the clearance between proximal sleeve section 12a and distal sleeve section 12b at joint 13, the possibility exists for leaks at the transition point from proximal sleeve section 12a to distal sleeve section 12b. In one embodiment, a resilient sealing member 65 is positioned between overlapping portions of proximal sleeve section 12a and distal sleeve section 12b to reduce or eliminate leaks at the transition point. In addition to providing a sealing function, sealing member 65 may act as a stop in that it will not allow the distal sleeve section 12b to escape the proximal sleeve section 12a, because the sealing member 65 will not fit past the reduced inside diameter of proximal sleeve section 12a or the enlarged outside diameter of distal sleeve section 12b. Sealing member 65 may be formed of any suitable material, and is preferably formed of a resilient polymer material such as fluorinated ethylene-propylene (FEP), polyester or silicone.

Figure 4A:
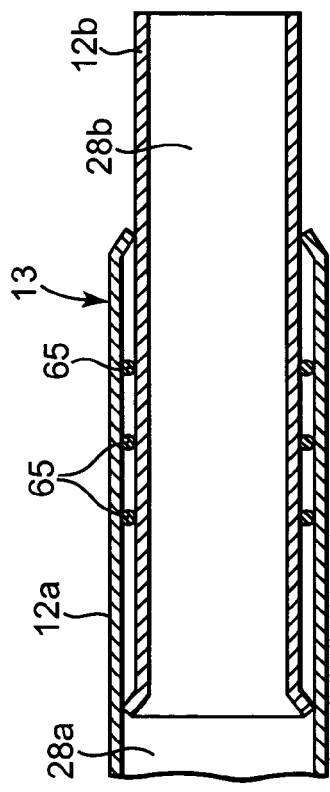
FIGS. 4A-4C are greatly enlarged schematic sectional views showing further embodiments of a telescoping joint and sealing member according to the invention.
Figure 4B:
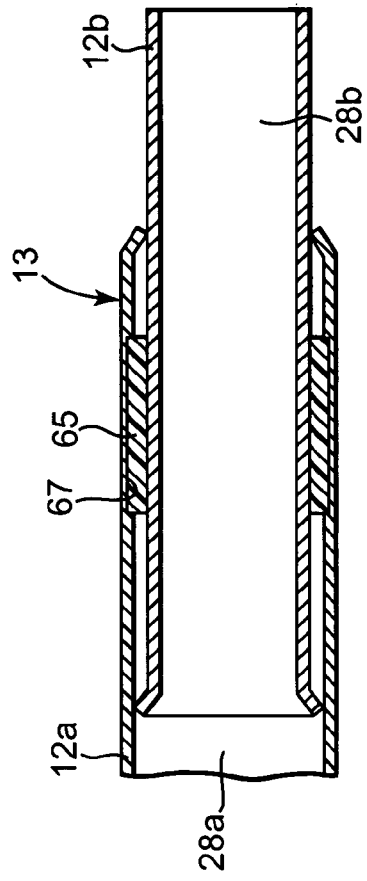
Figure 4C:
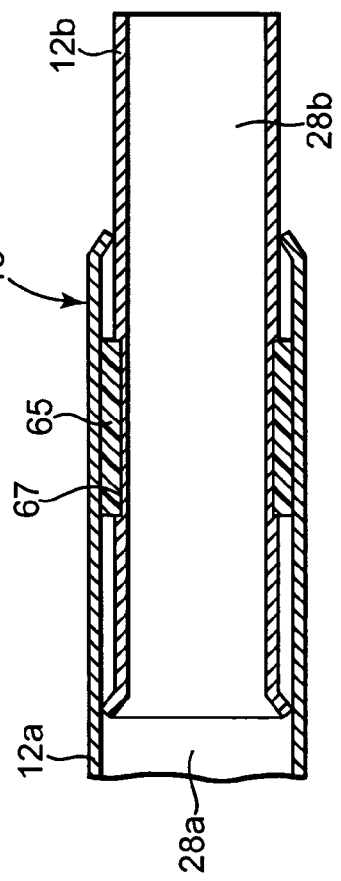

Although illustrated in FIG. 3 as having an elongated rectangular cross-section, sealing member 65 may have other cross-sectional profiles, such as circular. Additionally, there may be more than one sealing member 65 positioned between proximal sleeve section 12a and distal sleeve section 12b, such as the plurality of o-ring type sealing members illustrated in FIG. 4A. In one embodiment, sealing member 65 may be seated in a groove 67, either on the outside diameter of distal sleeve section 12b (see FIG. 4B), or on the inside diameter of proximal sleeve section 12a (see FIG. 4C). In another embodiment, the sealing member 65 of FIG. 3 may be a layer of silicone grease between proximal sleeve section 12a and distal sleeve section 12b. Alternately, sealing member 65 may be a resilient polymer material as described above, in combination with a silicone grease.

Is should be noted that although sleeve member 12 is depicted herein as having two telescoping sleeve sections (proximal sleeve section 12a and distal sleeve section 12b), in other embodiments sleeve member 12 may comprise any number of telescoping sleeve sections. Additional sleeve sections may be joined in telescoping engagement as described with reference to FIGS. 3-4C.

The distal portion 66 of the distal sleeve section 12b is configured to enable irrigating fluid to flow onto the viewing end of the endoscope and thereby flush debris from the viewing end of the endoscope. The distal portion 66 may be configured to resemble any of the endoscope sheath embodiments known to one skilled in the art, and in particular the distal portions of endoscope sheaths used in the Xomed® Endoscrub® lens cleaning system. Exemplary embodiments for distal portion 66 are shown and described in U.S. Pat. Nos. 5,989,183 and 6,110,103, which are commonly assigned herewith and hereby incorporated by reference. Exemplary embodiments for distal portion 66 are described in greater detail below.

Referring to FIGS. 5 and 6, distal portion 66 of the distal sleeve section 12b includes a terminal annular flange 68 that defines a circular end opening 70. The opening 70 is of smaller diameter than the outside diameter of the endoscope shaft 36 to prevent the shaft 36 from extending beyond the terminal flange 68. The flange 68 is also sized and shaped to avoid obstructing the field of view of the endoscope shaft 36.

The terminal flange 68 makes an angle of approximately 90° with an elongated axis 72 of the sleeve member 12 and is formed with three spacer dimples 76, 78 and 80, spaced approximately 120° apart. The dimples 76, 78 and 80, which can be formed by indentation, project approximately 0.005 to 0.020 inches from an inner surface 82 of the flange 68. This results in a distal gap or end space 100 in the size range of 0.005 to 0.020 inches.

Although the number of dimples provided on the flange 68 is preferably three, a greater or lesser number can be used, such as 1 to 10. The shape of the dimples 76, 78, and 80 can be round, triangle, or any other configuration which projects the specified amount from the inner surface 82.

In using the disposable sheath 10, the proximal sleeve section 12a and distal sleeve section 12b are positioned in a retracted position to create an initial receiving length for sheath 10, where the initial receiving length is shorter than the endoscope to be used. The distal end portion 38 of the endoscope shaft 36 is aligned with the recess 24 of the sleeve housing 16 and inserted through the bore 26 of the body portion 20 into the hollow interior 28 of the sleeve member 12.

The internal diameter of the bore 26 and the internal diameter of the proximal sleeve section 12a and distal sleeve section 12b are of greater magnitude than the outside diameter of the endoscope shaft 36 by a predetermined amount of approximately 0.002 inches to 0.012 inches. The diametrical difference between the bore 26 and the shaft 36, between the proximal sleeve section 12a interior 28a and the shaft 36, and between the distal sleeve section 12b interior 28b and the shaft 36 establishes a substantially annular irrigation channel or space 86 which extends from the fluid passage 54 in the collar 18 to the distal end portion 66 of the distal sleeve section 12b.

Referring to FIGS. 2 and 5, the length of the endoscope shaft 36 is measured from a terminal end 92 at the housing 32 to an opposite terminal end 94 at the distal end portion 38. The terminal end 94 is also referred to as the viewing end or the tip of the endoscope.

The disposable sheath 10 has a receiving length for the endoscope shaft 36 within the bore 26 and within the sleeve member 12. The receiving length for the endoscope shaft 36 is measured from a base 96 of the recess 24 to the crests 98 of the spacer dimples 76, 78 and 80 on the terminal flange 68 of the sleeve member 12. The length of the receiving length of sheath 10 will vary between its fully retracted (i.e., shortest) position and its fully extended (i.e., longest) position.

The sheath 10 operates compatibly with the endoscope 32 when the endoscope shaft 36 is longer than the receiving length of the sheath 10. Thus, the proximal sleeve section 12a and distal sleeve section 12b are initially positioned to create an initial receiving length for sheath 10 that is shorter than length of the endoscope to be used. Full insertion of the shaft 36 in the sheath 10 will cause the terminal end 94 of the endoscope shaft 36 to bottom against or engage the dimples 76, 78 and 80, and will then cause distal sleeve section 12b to telescope out from proximal sleeve section 12a and thereby extend the receiving length of sheath 10, until the endoscope housing 32 bottoms against the base surface 96 of the recess 24, as shown in FIG. 2. In this manner, the receiving length of sheath 10 matches the length of the endoscope, and yoke member 42 may securely hold the endoscope housing light port to prevent rotation of the endoscope shaft 36.

Engagement between the terminal end 94 of the endoscope shaft 36 and the dimples 76, 78 and 80 is assured for a multiplicity of different endoscope shafts that are longer than the initial retracted shaft receiving length of the sheath 10, up to the fully extended shaft receiving length of the sheath 10. Thus the length of sheath 10 precisely matches the length of endoscope 34, since the length of sheath 10 is continuously adjustable between its fully retracted and fully extended lengths. Under this arrangement a predetermined distal gap or end space 100 (FIG. 5) is established between the terminal end 94 of the endoscope shaft 36 and the annular flange 82 of the sleeve member 12, for any number of different endoscope shaft lengths that bottom against the dimples 76, 78 and 80.

Irrigation fluid such as saline is pumped or pulsed in any suitable known manner through the irrigation tube 52 to the fluid passage 54 and into the annular irrigation channel 86. The channel 86 extends through the bore 26 of the body portion 20 and through the interior 28 of the sleeve member 12 for communication with the end opening 70 of the sleeve member 12.

Before irrigation fluid in the irrigation channel 86 is expelled through the end opening 70, it is diverted through the distal gap 100 across the terminal end 94 of the endoscope shaft 36 by the flange 68. The diverted irrigation fluid flushes surgical debris from the terminal end 94 of the endoscope shaft 36.

Since the dimples 76, 78 and 80 have a predetermined height or projection, they hold the terminal end 94 of the endoscope shaft 36 in a corresponding predetermined step-back position from the inner surface 82 of the flange 68 to provide the desired magnitude of the distal gap 100. Thus the distal gap 100 has a magnitude of approximately 0.005 to 0.020 inches and, in cooperation with the flange 68 at the distal end portion 66 of the distal sleeve section 12b, enable the flow of irrigation fluid from the annular irrigation channel 86 to be redirected across the terminal end 94 of the endoscope shaft 36. The redirected flow of irrigation fluid provides an optimum flushing action to remove any surgical debris that accumulates at the endoscope viewing tip during a surgical procedure.

The predetermined step-back of the endoscope tip 94 also facilitates suction removal of a fluid droplet from the endoscope viewing end 94. For example, in some instances a drop of irrigation fluid may be left at the viewing end 94 of the endoscope shaft 36 when a flush cycle is completed. Since a field of view is taken through the viewing end 94, the residual drop of irrigation fluid can impede vision through the endoscope. Thus a slight suction pulse at the irrigation tube 52 will draw the obscuring droplet of irrigation fluid back into the irrigation channel 86. The flange 68 facilitates suction of the droplet from the viewing end 94 of the endoscope shaft 36.

If desired, an anti-fogging coating can be provided at the viewing end of the endoscope to help assure complete retraction of irrigation fluid from the viewing end 94 of the endoscope shaft 36 during a suction pulse.

The size of the irrigation channel 86 and the wall thickness of the proximal sleeve section 12a and distal sleeve section 12b are selected to provide a minimally intrusive low profile endoscope sheath for the endoscope shaft. Furthermore, by limiting the size of the irrigation channel 86 to the specified size range, irrigation solution passing into the annular channel 86 tends to remain stationary when the pumping or pulsing of irrigation fluid does not drip uncontrollably out of the end opening 70 when irrigation activity ceases.

The preferred size of the irrigation channel 86 is not intended to accommodate suction removal of surgical debris from the surgical site or from the viewing end 94 of the endoscope. Removal of surgical debris by suction generally requires a channel having a size that might permit irrigation fluid to drip from the sheath when pumping ceases. Thus a combination irrigation and suction channel for removing surgical debris would normally be of a size that significantly increases the profile of the sheath.

Optionally, some or all of the inner surface of the bore 26 and/or the proximal sleeve section 12a and distal sleeve section 12b can be treated with a hydrophilic or other suitable coating to enhance retention of irrigation fluid when irrigation pump activity ceases. Alternatively, a fluid retention surface texture can be provided at the inner surface of the sheath 10 for fluid retention purposes.

For example, a selected portion of the inner surface 104 (FIG. 5) at the distal end 66 of the distal sleeve section 12b can include score marks, pits, protrusions, or an etched or rough surface, all of which are schematically shown at reference number 110, to help capture residual solution in the irrigation channel 86 when irrigation pump activity ceases.

When an endoscopically assisted surgical procedure is completed, the entire sheath 10 can be discarded along with the endoscope shaft 36. Thus there is no need to engage in time consuming, inconvenient and expensive sterilization procedures.

Another embodiment of the disposable sheath for an endoscope is generally indicated by the reference number 120 in FIGS. 7 and 8. The sheath 120 includes a distal sleeve section 122 joined to a proximal sleeve section (not shown) that is identical to the proximal sleeve section 12a. The joining arrangement between the distal sleeve section 122 and proximal sleeve section 12a of this and other embodiments of the invention is identical to that illustrated in FIGS. 3-4C.

The sleeve section 122 has a distal portion 124 with a terminal end 126 that is inclined to the longitudinal axis 128 of the distal sleeve section 122, at an angle of approximately 5° to 70°. The terminal end 152 of an endoscope shaft 150 is inclined at an angle similar to that of the terminal end of the distal sleeve section 122.

As most clearly shown in FIG. 8, the flange 130 has a circumferential range of less than 360° with respect to the center of the distal sleeve section 122. Preferably the flange 130 has a circumferential range of approximately 90°-180° that encompasses the lowest portion of the inclined terminal end 126 as shown in FIG. 7.

The flange 130 includes a curved inner edge 132 and a pair of spacer dimples 136 and 138 that project a predetermined amount from an inner surface 140 of the flange 130. The dimples 136 and 138 project an amount that is equivalent to the projection specified for the dimples 76, 78 and 80 of the distal sleeve section 12b.

An end opening 144 is defined between the curved inner edge 132 of the flange 130 and a wall 146 of the distal sleeve section 122. The flange 130 is sized to interfere with a distal portion 148 of the endoscope shaft 150 that is inserted in the distal sleeve section 122, to prevent the shaft 150 from extending beyond the opening 144 of the distal sleeve section 122. The flange 130 is also sized and shaped to avoid obstructing the field of view of the endoscope shaft 150.

The spacer dimples 134 and 136 are located in a predetermined position on the flange 130 to engage the terminal end 152 of the endoscope shaft 150. Such engagement results in a step-back of the terminal end 152 from the inner surface 140 by the amount previously specified for the sheath 10. The step-back of the terminal end 152 of the endoscope shaft 150 from the inner surface 140 of the flange 130 establishes a distal gap or space 154 of corresponding magnitude between the terminal end 152 and the inner surface 140.

In using the sheath 120, the endoscope shaft 150 is inserted into the sleeve housing (not shown) and into the retracted sheath 120 in a manner similar to that described for the sheath 10. A substantially annular irrigation channel or space 158 dimensionally similar to the irrigation channel 86 is established between the endoscope shaft 150 and the sheath 120. The terminal end 152 of the endoscope shaft engages the spacer dimples 136 and 138, to establish the distal gap 154.

Irrigating fluid that is pulsed or pumped into the irrigation channel 158 from the sleeve housing (not shown), exits from the distal sleeve section 122 through the end opening 144. Some portions of the irrigation fluid that exit from the end opening 144 are diverted across the terminal end 152 of the endoscope shaft 150 by the flange 130. Other portions of irrigation fluid that do not impinge on the flange 130 can flow onto the terminal end 152 because of the optimum size of the distal gap 154.

The movement of fluid across the terminal end 152 of the endoscope shaft 150 provides a flushing action at the terminal end that cleans away any surgical debris. Similarly, the flange 130 facilitates suction of irrigation fluid droplets from the terminal end 152 of the endoscope shaft 150 to prevent obscuring of the field of view by any irrigation fluid that accumulates thereon.

The sheath 120 otherwise operates in a manner similar to that previously described for the sheath 10.

It should be noted that the step-back of the endoscope shaft 150 from the terminal end 126 provided by the dimples 136 and 138 is not a necessity on flange 130 with distal portions inclined in the range of approximately 25 degrees to 70 degrees because the flange 130 holds the endoscope shaft 150 back from the terminal end 126. Irrigation fluid can thus exit from the distal sleeve section 122 at the end opening 144. If desired, the flange 130 can have a 360 degree range and in this case, spacer dimples such as 136 and 138 would be desirable.

Figure 9:
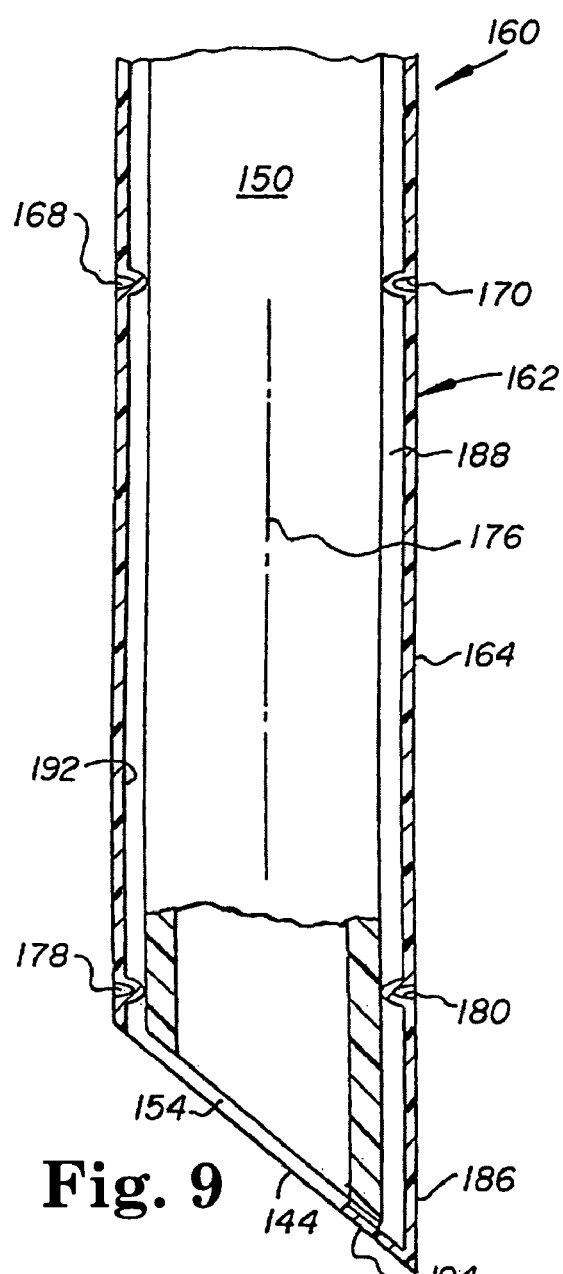
Figure 10:
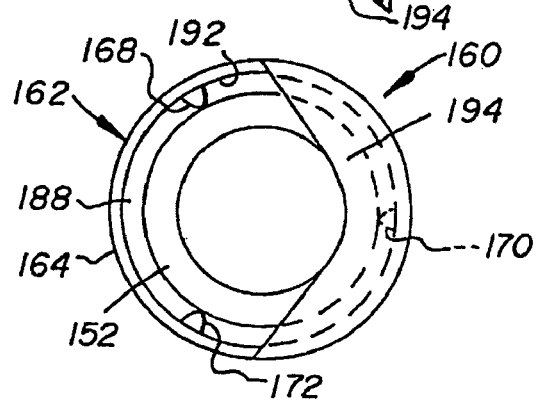

A further embodiment of the disposable sheath for an endoscope is generally indicated by the reference number 160 in FIGS. 9 and 10. The sheath 160 includes a distal sleeve section 162 joined to a proximal sleeve section (not shown) that is identical to the proximal sleeve section 12a.

The sleeve section includes a tubular wall 164 having a set of centering dimples such as 168, 170 and 172 spaced approximately 120 degrees apart and provided at a first axial location with respect to a longitudinal axis 176 of the distal sleeve section 162. A second set of similarly spaced centering dimples, such as the dimples 178 and 180, are provided at a second axial location proximate a distal portion 186 of the distal sleeve section 162. The axial spacing between the first and second set of centering dimples is approximately 1 to 5 inches.

If desired, the centering dimples can be provided in a non-opposed longitudinally staggered arrangement. It should also be noted that centering dimples can be provided on any of the sleeve members disclosed herein.

When the endoscope shaft 150 is disposed in the sheath 160, an annular irrigation channel 188 is established that is dimensionally similar to the irrigation channel 86.

The centering dimples 168, 170, 172 and 178, 180 project from an inner surface 192 by a predetermined amount that is less than the size of the irrigation channel and help center the endoscope shaft 150 that is positioned in the distal sleeve section 162.

The distal sleeve section 162 also includes an end flange 194 similar to the end flange 130 of the distal sleeve section 122 with spacer dimples (not shown) similar to the spacer dimples 136 and 138.

As an alternative to the centering dimples 168, 170, 172, 178 and 180, the distal sleeve section 162 can include axially elongated centering projections (not shown) that extend the entire axial distance of the sleeve member wall 164 or a portion of the axial distance to provide a centering function similar to that provided by the centering dimples.

In all other respects the structure and operation of the sheath 160 including the distal sleeve section 162 are similar to those of the sheaths 10 and 120.

Figure 11:
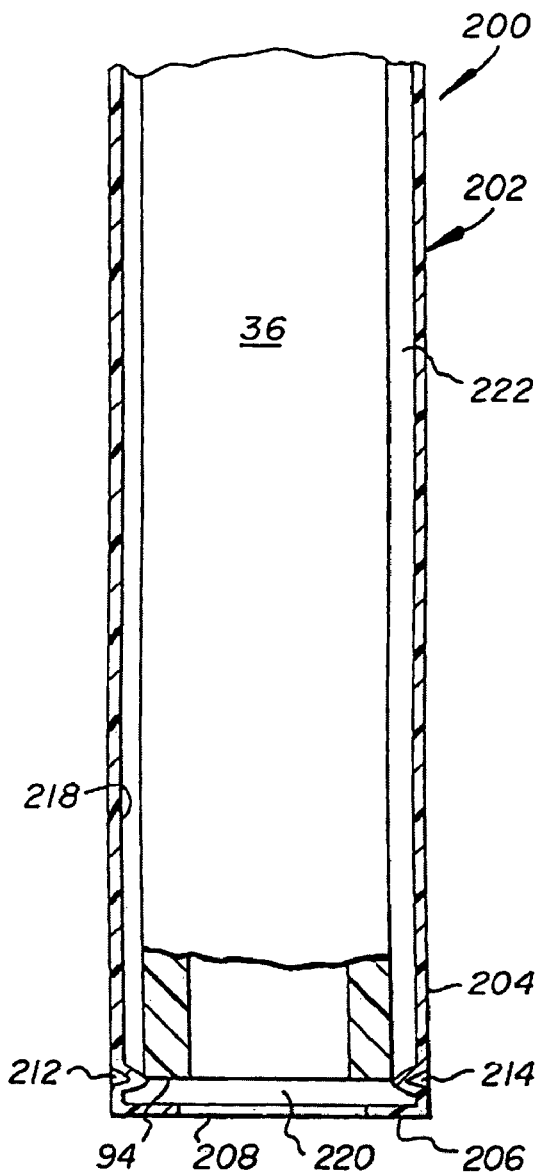
Figure 12:
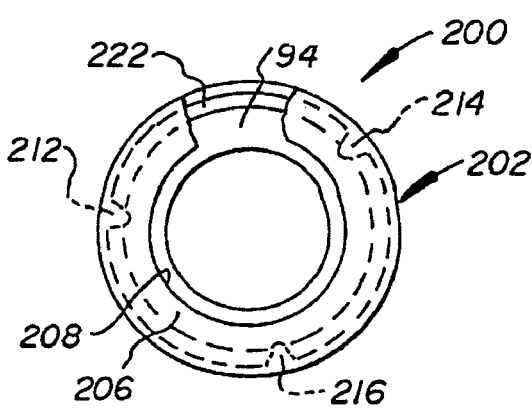

Still another embodiment of the disposable sheath for an endoscope is generally indicated by the reference number 200 in FIGS. 11 and 12. The sheath 200 includes a distal sleeve section 202 joined to a proximal sleeve section (not shown) that is identical to the proximal sleeve section 12a.

The distal sleeve section 202 includes a distal portion 204 having an annular terminal end flange 206 that defines an end opening 208. A set of spacer dimples 212, 214 and 216 spaced approximately 120 degrees apart are provided proximate the end flange 206. The projection of the spacer dimples 212, 214 and 216 from an inside surface 218 of the distal sleeve section 202 interferes with the endoscope shaft 36 to prevent passage of the terminal end portion 94 of the endoscope shaft 36 beyond the spacer dimples 212, 214 and 216.

The spacer dimples 212, 214 and 216 are at a predetermined location that establishes a gap 220 of similar magnitude to the gap 100 between the endoscope terminal end 94 and the sleeve member end flange 206. The spacer dimples 212, 214 and 216 and the end flange 206 are also of a size that avoids obscuring the field of view through the endoscope end 94.

A substantially annular irrigation channel 222, dimensionally similar to the irrigation channel 86 of the sheath 10, is established between the endoscope shaft 36 and the inner surface 218 of the sheath 200. Except for the distal portion 204, the distal sleeve section 202 is structurally similar to the sleeve section 12b.

In using the sheath 200, irrigation fluid (not shown) is directed into the irrigation channel 222 for exit at the end opening 208. Before the irrigation fluid exits from the opening 208, it enters the distal gap 220 and is diverted across the endoscope end 94 by the flange 206. The diverted fluid flushes debris from the endoscope end 94 to provide an effective cleaning action. Other aspects of the structure and operation of the sheath 200 are similar to those previously described for the sheath 10.

A still further embodiment of a disposable endoscope sheath is generally indicated by the reference number 230 in FIGS. 13 and 14. The sheath 230 includes a distal sleeve section 232 joined to a proximal sleeve section (not shown) that is identical to the proximal sleeve section 12a.

The distal sleeve section 232 includes a distal portion 234 having a terminal end 236 inclined to a longitudinal axis 238 of the distal sleeve section 232. The inclination of the terminal end 236 to the longitudinal axis 238 is in the same angular range as that of the flange 130 in the distal sleeve section 122. An end opening 240 is defined at the terminal end 236.

A set of spacer dimples 244, 246 and 248 spaced approximately 120 degrees apart as shown in FIG. 12, project from an inside surface 250 of the distal sleeve section 232 to prevent passage of the terminal end portion 152 of the endoscope shaft 150 beyond the spacer dimples.

A distal gap 254, similar in magnitude to the distal gap 100 of the sheath 10, is thus established between the endoscope terminal end 152 and the sleeve member terminal end 236. The spacer dimples 244, 246 and 248 are of a size that avoids obscuring the field of view through the endoscope end 152.

Although the distal portion 234 has an inclined end 236, the general arrangement of the spacer dimples 244, 246 and 248 is similarly adaptable to a non-inclined terminal end arrangement.

An irrigation channel 256, dimensionally similar to the irrigation channel 86 of the sheath 10, is established between the endoscope shaft 150 and the inner surface 250 of the distal sleeve section 232. Except for the distal portion 234, the distal sleeve section 232 is structurally similar to the distal sleeve section 122 of the sheath 120.

In using the sheath 230, irrigation fluid directed into the irrigation channel 256 exits at the end opening 240. The exiting fluid tends to flow onto the endoscope end 152 due to optimal retraction of the endoscope end 152 within the distal sleeve section 232. Fluid can thus flow into the gap 254 and onto the endoscope end 152 thereby flushing debris from the endoscope end to provide an effective cleaning action. The sheath 230 is otherwise operationally similar to the sheath 120.

Another embodiment of the disposable endoscope sheath is generally indicated by the reference number 260 in FIGS. 15 and 16. The sheath 260 includes a distal sleeve section 262 joined to a proximal sleeve section (not shown) that is identical to the proximal sleeve section 12a.

The distal sleeve section 262 includes a distal portion 264 having diametrically opposite flange portions 266 and 268 that define an end opening 270. The end flanges 266 and 268 are sized to prevent passage of the terminal end portion 94 of the endoscope shaft 36 beyond the end opening 270 without obscuring the field of view through the endoscope end 94.

A substantially annular irrigation channel 276 dimensionally similar to the irrigation channel 86 of the sheath 10 is defined between the endoscope shaft 36 and the inner surface 272 of the distal sleeve section 262.

Except for the distal portion 264, the distal sleeve section 262 is structurally similar to the distal sleeve section 12b.

In using the sheath 260, irrigation fluid directed into the irrigation channel 276 exits at the end opening 270. As irrigation fluid exits from the end opening 270, it can flow onto the endoscope end 94 due to the predetermined recession of the shaft 36 in the distal sleeve section 262 and flush surgical debris from the endoscope end 94, thereby providing an effective cleaning action.

If desired, dimples (not shown) similar to the dimples of the distal sleeve sections 12b and 122, can be provided at the end flanges 266 and 268 to establish a specified predetermined gap between the endoscope end 94 and the end flanges 266 and 268. In this manner, irrigation fluid can be diverted across the endoscope end 94 by the flanges 266 and 268 to flush away surgical debris from the endoscope end 94.

Figure 17:
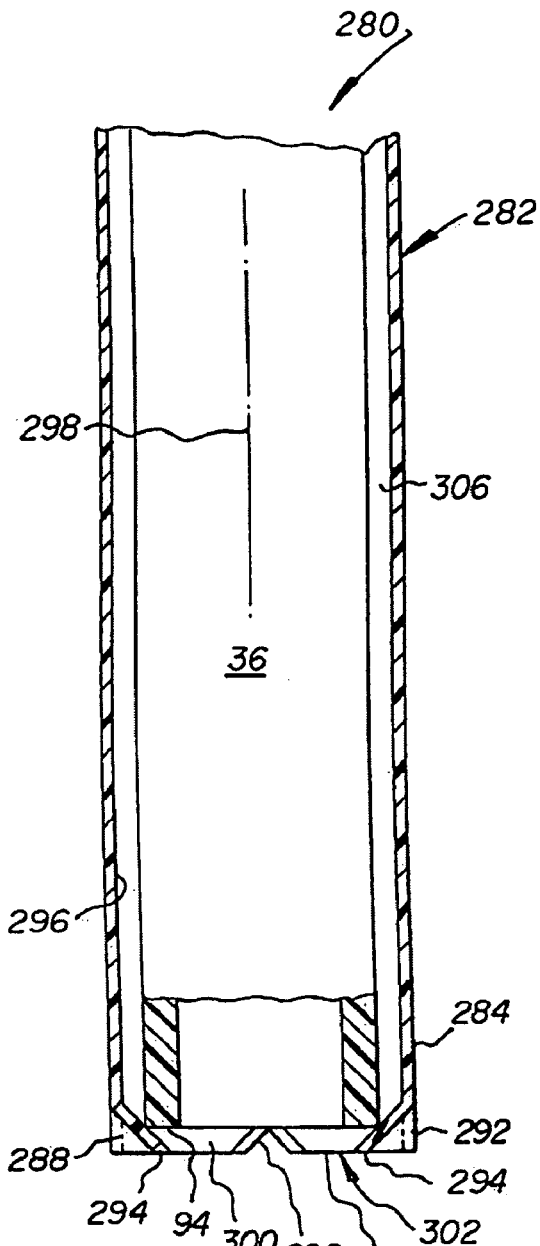
Figure 18:
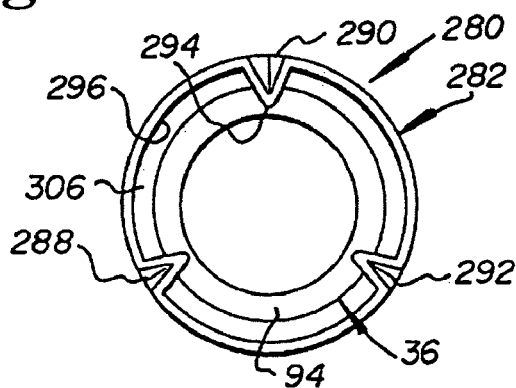

Another embodiment of a disposable endoscope sheath is generally indicated by the reference number 280 in FIGS. 17 and 18. The sheath 280 includes a distal sleeve section 282 joined to a proximal sleeve section (not shown) that is identical to the proximal sleeve section 12a.

The distal sleeve section 282 includes a distal portion 284 with terminal deformations 288, 290 and 292 spaced approximately 120 degrees apart. The deformations 288, 290 and 292 are V-shaped in end view as shown in FIG. 16 and can be inclined approximately 20 degrees to 90 degrees as shown in FIG. 15. It should be noted that the number of deformations used can be as few as one or as many as 30.

A tip portion 294 of the deformations 288, 290 and 292 extends from an inner wall surface 296 of the distal sleeve section 282 toward an axis 298 an amount that prevents passage of the terminal end portion 94 of the endoscope shaft 36 beyond the deformations 288, 290 and 292 without obscuring the field of view through the endoscope end 94.

The angle of the deformations 288, 290 and 292 and the extent of the tip portions 294 are also selected to provide a distal gap 300 that is dimensionally similar to the gap 100 between the endoscope terminal end 94 and a terminal end 302 of the distal sleeve section 282.

A substantially annular irrigation channel 306, dimensionally similar to the irrigation channel 86 of the sheath 10, is established between the endoscope shaft 36 and the inner surface 296 of the distal sleeve section 282. Except for the distal portion 284, the distal sleeve section 282 is structurally similar to the distal sleeve section 12*b*.

In using the sheath 280, irrigation fluid directed into the irrigation channel 306 exits at an end opening 308 of the distal sleeve section 282. The exiting fluid flows onto the endoscope end 94 to provide an effective cleaning action. The distal gap 300, being within the predetermined size range, helps assure the effectiveness of the flushing action.

Figure 19:
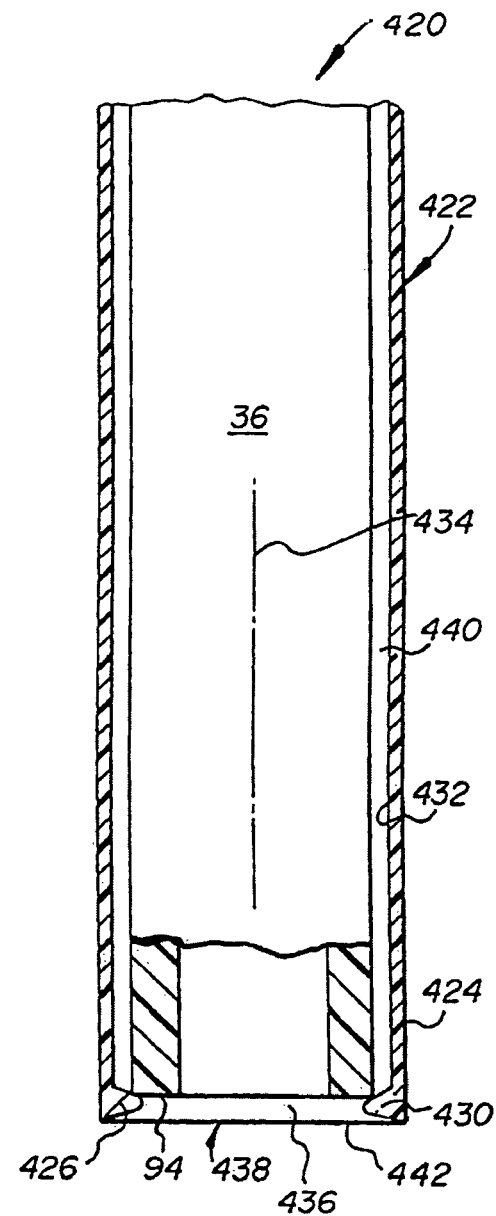
Figure 20:
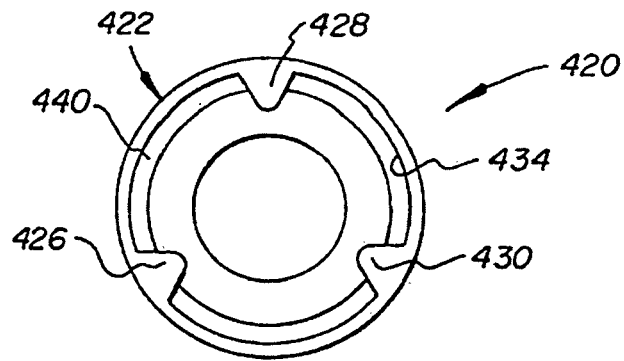

Another embodiment of a disposable endoscope sheath is generally indicated by the reference number 420 in FIGS. 19 and 20. The sheath 420 includes a distal sleeve section 422 joined to a proximal sleeve section (not shown) that is identical to the proximal sleeve section 12*a*.

The distal sleeve section 422 includes a distal portion 424 with terminal dimples 426, 428 and 430 spaced approximately 120 degrees apart. The dimples 426, 428 and 430 can be molded or formed by indentation.

The dimples 426, 428 and 430 extend from an inner wall surface 432 of the distal sleeve section 422 toward an axis 434 an amount that prevents passage of the terminal end portion 94 of the endoscope shaft 36 beyond the dimples 426, 428 and 430 without obscuring the field of view through the endoscope end 94.

The dimples 426, 428 and 430 are also formed to provide a distal gap 436 that is dimensionally similar to the gap 100 between the endoscope terminal end 94 and a terminal end 438 of the distal sleeve section 422.

A substantially annular irrigation channel 440, dimensionally similar to the irrigation channel 86 of the sheath 10, is established between the endoscope shaft 36 and the inner surface 432 of the distal sleeve section 422. Except for the distal portion 424, the distal sleeve section 422 is structurally similar to the distal sleeve section 12*b*.

In using the sheath 420, irrigation fluid directed into the irrigation channel 440 exits at an end opening 442 of the distal sleeve section 422. The exiting fluid flows onto the endoscope end 94 to provide an effective cleaning action. The distal gap 436, being within the predetermined size range, assures effective flushing action.

Although this embodiment and other embodiments disclosed herein show the use of three dimples, it should be noted that as few as one or as many as 10 dimples can be used.

Some advantages of the invention evident from the foregoing description include a disposable sheath that enables the endoscope to be positioned at an optimum location with respect to a sleeve. The endoscope can be slightly recessed in some embodiments, or flush with the terminal end of the sleeve in other embodiments. The sleeve member of the sheath is a low profile structure and thus does not require any significant enlargement of a surgical incision to accommodate the endoscope and sleeve. A further advantage is that the sleeve member need not be customized to different lengths of an endoscope and can accommodate a variety of different endoscope lengths. The sleeve can also be adapted to accommodate endoscopes with barrels that differ in outside diameter by 0.001 to 0.005 inches. The disposable sheath is economical to manufacture and saves time and money by eliminating the need to use sterilizable components. The invention is also adaptable to endoscopes that have inclined or non-inclined terminal portions.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiments shown and described without departing from the scope of the present invention. This application is intended to cover any adaptations or variations of the preferred embodiments discussed herein. Therefore, it is manifestly intended that this invention be limited only by the claims and the equivalents thereof.

What is claimed is:

1. A disposable sheath for an endoscope having an endoscope housing and an endoscope shaft that extends from the endoscope housing, wherein the endoscope shaft has a viewing end and wherein the disposable sheath comprises:
   a disposable extendable sleeve sized to accommodate the endoscope shaft, the disposable extendable sleeve having a proximal sleeve section, a distal sleeve section and a collar portion, the proximal sleeve section and distal sleeve section comprising separate and individual sections joined in telescoping arrangement to provide the disposable extendable sleeve a variable length, wherein the collar portion is attached to the proximal sleeve section;
   a distal portion of the disposable extendable sleeve having an inwardly directed terminal flange that is configured to engage the viewing end of the endoscope shaft and prevent extending of the viewing end of the endoscope shaft distal a terminal end of the disposable extendable sleeve such that insertion of the endoscope shaft into the disposable extendable sleeve causes the distal sleeve section to telescope distally away from the proximal sleeve section and thereby adjusts the length of the disposable extendable sleeve as the disposable extendable sleeve receives the endoscope shaft, the distal portion of the disposable extendable sleeve further configured to direct irrigation fluid onto the viewing end of the endoscope to flush surgical debris from the viewing end of the endoscope; and
   a distal end of the collar portion having a recess that is adapted to receive a portion of the endoscope housing.

2. The sheath of claim 1, wherein a distal end of the proximal sleeve section has a reduced inside diameter, and a proximal end of the distal sleeve section has an enlarged outside diameter, wherein the reduced inside diameter of the proximal sleeve section is smaller than the enlarged outside diameter of the distal sleeve section.

3. The sheath of claim 2, wherein the proximal end of the distal sleeve section is shaped to guide the endoscope into the distal sleeve section.

4. The sheath of claim 1, further comprising a sealing member positioned between overlapping portions of the proximal sleeve section and the distal sleeve section.

5. The sheath of claim 4, wherein the sealing member comprises a resilient material.

6. The sheath of claim 5, wherein the sealing member comprises a plurality of o-rings.

7. The sheath of claim 4, wherein the sealing member comprises a grease.

8. The sheath of claim 1, wherein the proximal sleeve section and the distal sleeve section are of generally circular cross section with predetermined inner diameters, such that an annular irrigation space of predetermined size is defined between the proximal sleeve section and the endoscope shaft and between the distal sleeve section and the endoscope shaft when the proximal sleeve section and distal sleeve section receive the endoscope shaft.

9. The sheath of claim 8, wherein the irrigation fluid is directed from the irrigation space onto the viewing end of the endoscope.

10. The sheath of claim 7, wherein the annular irrigation space is sized to retain the irrigation solution by means of surface tension when the irrigation fluid is no longer being directed into the irrigation space.

11. The sheath of claim 10, wherein the annular irrigation space ranges in size from about 0.002 inches to about 0.012 inches.

12. The sheath of claim 7, wherein the distal portion of the disposable extendable sleeve has an inner surface, the inner surface having formations selected from the group consisting of coatings, score marks, pits, etching and roughness to provide the inner surface with hydrophilic or irrigation fluid retention characteristics.

13. The sheath of claim 1, wherein the distal portion of the disposable extendable sleeve includes a spacer member to maintain the viewing end of the endoscope in a predetermined position relative to the terminal end of the disposable extendable sleeve.

14. The sheath of claim 13, wherein the spacer member establishes a distal gap between the viewing end of the endoscope and the terminal end of the disposable extendable sleeve.

15. The sheath of claim 14, wherein the distal gap ranges from about 0.005 inches to about 0.020 inches.

16. The sheath of claim 1, wherein a distal terminal end of the disposable extendable sleeve is inclined at an angle ranging from 5 degrees to 90 degrees to the longitudinal axis of the disposable extendable sleeve.

17. The sheath of claim 1, wherein the proximal sleeve section and distal sleeve section are formed of a rigid material.

18. The sheath of claim 1, wherein the distal portion of the disposable extendable sleeve has at least one opening to direct irrigation fluid onto the viewing end of the endoscope.

19. The disposable sheath of claim 1, wherein the disposable extendable sheath further comprises a body portion that depends from the collar portion so that the body portion is intermediate the collar portion and the proximal sleeve section.

20. The disposable sheath of claim 1, and further comprising an irrigation fitting joined to the collar portion to provide fluid communication with a bore extending in the disposable extendable sleeve.

21. A disposable sheath for an endoscope having an endoscope housing and an endoscope shaft that extends from the endoscope housing, wherein the endoscope shaft has a viewing end and wherein the disposable sheath comprises:

a disposable telescoping sleeve having a proximal sleeve section, a distal sleeve section and a collar portion, the proximal sleeve section and distal sleeve section comprising separate and individual sections joined in telescoping arrangement, the disposable telescoping sleeve having a length varying between a fully retracted length and a fully extended length, the proximal sleeve section and the distal sleeve section sized to accommodate therein the endoscope shaft and having a generally circular cross section with a longitudinal axis and a predetermined inner diameter, such that a predetermined irrigation space is defined between the proximal sleeve section and the endoscope shaft and between the distal sleeve section and the endoscope shaft when the disposable telescoping sleeve receives the endoscope shaft, wherein the collar portion is attached to the proximal sleeve section;

a distal portion of the distal sleeve section having an inwardly directed terminal flange configured to engage the viewing end of the endoscope shaft and prevent extending of the viewing end of the endoscope shaft distal a terminal end of the disposable telescoping sleeve such that insertion of the endoscope shaft into the disposable telescoping sleeve causes the distal sleeve section to telescope distally away from the proximal sleeve section and thereby adjusts the length of the disposable telescoping sleeve as the disposable telescoping sleeve receives the endoscope shaft, and the distal portion of the disposable telescoping sleeve further configured such that irrigating solution directed into the irrigation space is redirected by the distal portion to flow onto the viewing end of the endoscope to flush surgical debris from the viewing end of the endoscope; and a distal end of the collar portion having a recess that is adapted to receive a portion of the endoscope housing.

22. The sheath of claim 21, wherein the terminal flange directs irrigation solution onto the viewing end of the endoscope.

23. The sheath of claim 22, wherein the distal portion of the distal sleeve section further includes dimples for stepping the viewing end of the endoscope away from the terminal flange by a predetermined distance.

24. The sheath of claim 22, wherein the terminal flange has a circumferential range of less than 360 degrees with respect to the longitudinal axis.

25. The disposable sheath of claim 21, wherein the disposable extendable sheath further comprises a body portion that depends from the collar portion so that the body portion is intermediate the collar portion and the proximal sleeve section.

26. The disposable sheath of claim 21, and further comprising an irrigation fitting joined to the collar portion to provide fluid communication with a bore extending in the disposable telescoping sleeve.

27. A method of cleaning surgical debris from the viewing end of an endoscope comprising:

providing an endoscope having an endoscope housing and an endoscope shaft that extends from the endoscope housing, wherein the endoscope shaft has a viewing end, wherein the endoscope shaft has a length;

providing a disposable endoscope sheath having a disposable telescoping sleeve for receiving the endoscope shaft, the disposable telescoping sleeve comprising a proximal section, a distal section and a collar portion, wherein the proximal and distal sections are joined in telescoping arrangement and having an inner diameter sized to establish an irrigation space between the disposable telescoping sleeve and the endoscope shaft, with the viewing end of the endoscope shaft positioned within a distal portion of the disposable telescoping sleeve, wherein an end of the distal section opposite the proximal section has an inwardly directed terminal flange extending therefrom, wherein the collar portion is attached to the proximal section and wherein a distal end of the collar portion has a recess;

arranging the proximal and distal sections of the disposable telescoping sleeve in a retracted position having a length shorter than a length of the endoscope shaft;

inserting the endoscope shaft into the sheath with the disposable telescoping sleeve in the retracted position;

engaging the terminal flange with the viewing end of the endoscope shaft to prevent insertion of the viewing end of the endoscope shaft beyond a terminal end of the disposable telescoping sleeve;

adjusting the disposable telescoping sleeve to a length approximately equal to the length of the endoscope shaft by continuing to insert the endoscope shaft into the sheath, wherein the engagement of the viewing end of the endoscope with the terminal flange causes the distal sleeve section to telescope distally away from the proximal sleeve section;

extending a portion of the endoscope housing into the recess at the distal end of the collar portion; and directing irrigation fluid into the irrigation space at a proximal end of the disposable telescoping sleeve for movement toward the viewing end of the endoscope shaft and onto the viewing end to flush away surgical debris from the endoscope shaft.

28. The method of claim 27, further comprising:
providing the disposable telescoping sleeve with an inside diameter that together with the outside of the endoscope shaft enables the irrigation space to retain irrigation fluid by capillary action when the irrigation fluid is no longer being directed into the irrigation space.

29. The method of claim 27, further comprising:
initiating a suction pulse to draw droplets of irrigation fluid back into the irrigation space after directing irrigation fluid onto the viewing end of the endoscope shaft.

30. The method of claim 27, wherein the disposable extendable sheath further comprises a body portion that depends from the collar portion so that the body portion is intermediate the collar portion and the proximal sleeve section.

31. The disposable sheath of claim 27, and further comprising an irrigation fitting joined to the collar portion to provide fluid communication with a bore extending in the disposable telescoping sleeve.

* * * * *

UNITED STATES PATENT AND TRADEMARK OFFICE
CERTIFICATE OF CORRECTION

| | | |
|---|---|---|
| PATENT NO. | : 7,811,228 B2 | Page 1 of 1 |
| APPLICATION NO. | : 10/899209 | |
| DATED | : October 12, 2010 | |
| INVENTOR(S) | : Kenneth M. Adams | |

It is certified that error appears in the above-identified patent and that said Letters Patent is hereby corrected as shown below:

Column 13, line 9, delete "claim 7" and insert in place thereof --claim 8--.

Column 13, line 16, delete "claim 7" and insert in place thereof --claim 8--.

Signed and Sealed this
Eighth Day of March, 2011

David J. Kappos
*Director of the United States Patent and Trademark Office*